United States Patent [19]
Semancik et al.

[11] Patent Number: 5,330,855
[45] Date of Patent: Jul. 19, 1994

[54] PLANAR EPITAXIAL FILMS OF SNO2

[75] Inventors: Stephen Semancik, Mount Airy; Richard E. Cavicchi, Washington Grove, both of Md.

[73] Assignee: The United States of America, as represented by the Secretary of Commerce, Washington, D.C.

[21] Appl. No.: 764,203

[22] Filed: Sep. 23, 1991

[51] Int. Cl.$^5$ .............................. B32B 7/02
[52] U.S. Cl. .................. 428/701; 73/31.06; 428/216; 428/336; 428/469; 428/472; 428/702
[58] Field of Search .............. 428/446, 216, 336, 212, 428/469, 472, 701, 702; 73/31.06

[56] References Cited

U.S. PATENT DOCUMENTS

| | | | |
|---|---|---|---|
| 3,483,110 | 12/1969 | Rozgonyi | 204/192 |
| 3,745,071 | 7/1973 | Mitsui | 148/171 |
| 4,298,410 | 11/1981 | Nakajima et al. | 148/172 |
| 4,417,092 | 11/1983 | Moustakas et al. | 136/258 |
| 4,495,219 | 1/1985 | Kato et al. | 427/82 |
| 4,652,463 | 3/1987 | Peters | 427/53.1 |

OTHER PUBLICATIONS

"Preparation of Well-Ordered, Oxygen-Rich SNO2(110) Surfaces Via Oxygen Plasma Treatment", Cavicchi et al.; J. Vac. Sci. Technol. A8 (3), May/Jun. 1990; pp. 2347-2352.
"Oxygen Vacancies and Defect Electronic States on the SNO2(110)-1×1 Surface"; Cox et al.; Physico/-Review B; vol. 38, No. 3; Jul. 1988; pp. 2072-2083.
"Epitaxial Thin Films of ZNO on CDS and Sapphire"; Rozgonyi et al.; Jour. Vacuum Sci. and Tech., vol. 6, No. 1; pp. 115-119.
"High Rate Epitaxial Growth of ZNO Films on Sapphire by Planar Magnetron RF Sputtering System"; Shiosaki et al.; Jour. of Crystal Growth 45 (1978); pp. 346-349.
"Gas Sensing Characteristics of Reactivity Sputtered SNO2 Films"; Kuriki et al.; Elec. and Common in Japan, Part 2, vol. 70, No. 4, 1987, pp. 54-64.
"Ceramic Epitaxial Films and Multilayers Prepared by MOCVD"; Chang et al.; Proceedings of the 7th CIM-TEC World Ceramics Congress, Montecatini Terme, Italy, Jun. 24-30, 1990.
"Tin Dioxide Gas Sensors"; McAleer et al.; J. Chem. Soc., 1987; pp. 1323-1346.
"An Arsine Monitoring Device Using an Snox Thin Film"; Mokwa et al.; CH2127-9/85/0000-0389; 1985 IEEE; pp. 389-392.
"TIOX/AL2O3 Multilayer Ceramic Thin Films"; Alexander et al.; J. Am. Ceram. Soc., 73(6); 1990; pp. 1737-1743.
"Chemical Vapor Deposition of Antimony-Doped Tin Oxide Films formed From Dibutyl Tin Diacetate"; Kane et al.; J. Electrochem. Soc.; vol. 123, No. 2; pp. 270-277.
"Chemical Vapor Deposition of SNO2 Thin Films on Rutile Single Crystals"; Nagano; Journ. of Crystal Growth 67 (1984); pp. 639-644.
"Growth of Highly Oriented Tin Oxide Thin Films by Laser Evaporation Deposition"; Dai et al.; Appl. Phys. Lett. Oct. 1990; 1990; pp. 1879-1881.
"Epitaxy of TIO2 Thin Film of Sapphire by MOCVD"; Chang et al.; Mrs. Spring Meeting Symposium J, Thin Film Structures and Phase Stability, San Francisco, Calif., Apr. 16-21, 1990.
"Fundamental Studies of Epitaxial and Granular Tin Oxide Films"; Cavicchi et al.; Proceedings of the 3rd International Meeting on Chemical Sensors, Cleveland, Ohio, Sep. 24-27, 1990.

Primary Examiner—A. A. Turner
Attorney, Agent, or Firm—Fran S. Wasserman

[57] ABSTRACT

A planar epitaxial film of tin oxide has low defect density, high purity, crystalline rutile unit cell structure, one crystalline orientation, controlled stoichiometry, extended lateral dimensions, extremely smooth surface morphology, a high degree of atomic order extending to the surface of the film and is colorless and transparent. The film is made by a method which includes reactive sputter deposition. The films can be used in chemical sensors as well as in numerous other applications.

14 Claims, 6 Drawing Sheets

PLANAR EPITAXIAL FILMS OF SNO2

FIELD OF THE INVENTION

The present invention pertains to planar epitaxial films of semiconducting oxides and more particularly to planar epitaxial films of rutile structured semiconducting oxides on insulating substrates, methods for their production and chemical gas sensors comprised of these materials.

BACKGROUND OF THE INVENTION

A number of methods have been reported for producing tin oxide and related oxide materials. Powders have been produced and studied for a number of years. For certain applications, however, the advantages of films have made film deposition the fabrication method of choice.

The richness of the chemical, electronic and mechanical properties of oxide films has made them useful in a wide variety of applications. The majority of the technological films currently available are polycrystalline. Polycrystalline films result from processes which do not rigorously control the microstructure of the film during deposition. These films are textured and have distributions of varying crystalline structures, sizes, and orientation and a large number of grain boundaries. Additionally, while polycrystalline films of oxide having extended lateral dimension ($>1$ cm$^2$) have been obtained, highly ordered oxides have been generally limited to single crystals, the dimensions of which for many oxides are are typically less than about 1 cm$^2$.

Nagano in "Chemical Vapor Deposition of Tin Oxide Thin Films on Rutile Single Crystals", *J. Crystal Growth*, 67, 639-644 (1989), teaches the deposition of thin films of tin oxide on the surface of titanium oxide by chemical vapor deposition. Kane, et al., in "Chemical Vapor Deposition of Antimony Doped Tin Oxide Film Formed from Dibutyl Tin Diacetate", *J. Electrochem. Soc.: Solid State Science and Technology*, volume 123, Number 2, February, 1976, teaches a chemical vapor deposition process for preparing transparent conducting layers of antimony doped tin oxide utilizing dibutyl tin diacetate, antimony pentachloride, oxygen, water and nitrogen as a carrier gas at a substrate temperature of 400° to 550° C. This method was designed to fulfill a need for more highly conducting coatings than those obtainable without doping, while still possessing optical transmission in excess of 80% throughout the visible spectrum.

In "Growth of Highly Oriented Tin Oxide Thin Films by Laser Evaporation Deposition", *Appl. Phys. Lett.*, 57, 29 Oct. 1990, Dai et al. disclose conducting thin films of tin oxides which were prepared by the laser evaporation of a pressed polycrystalline undoped powder tin oxide onto unheated substrates. Kuriki et al. in "Gas sensing Characteristics of Reactively Sputtered SnO$_2$ Films", *Electronics and Communications in Japan*, Part 2, Vol. 70, No. 4, 1987, disclose gas sensors which are composed of polycrystalline SnO$_2$ films. In many cases imperfections in these oxides such as grain boundaries, surface steps, and oxygen vacancy defects set limits on the functionality of the film.

Nearly perfect (pure), stoichiometric, structurally ordered in both short and long range, smooth, crystal-like tin oxide films formed by heteroepitaxial growth would be expected to exhibit more uniform properties and interactions when presented to technological environments and stimuli, as for example gases, photons, and electrons. With only one crystalline orientation throughout and no defect sites the adsorption kinetics would be coherent across the film. Removing structural defects (large ones such as grain boundaries, or small ones such as individual vacancy sites), would produce a much more uniform optical density by removing random scattering sites for transparent conductors. Near perfection in such films could also be expected to yield higher mobilities in electronic transport and when the perfection extends out to the surface, it could allow unique control of frictional coefficients.

While the advantages of producing high quality completely epitaxial films of non-oxide materials has been widely recognized in the semiconductor industry, efforts to produce films at equivalent quality for oxide materials have largely been confined to research on the high temperature superconductor materials.

Chang et al. in "Ceramic Epitaxial Films and Multilayers Prepared by MOCVD", Proceedings of the 7th CIMTEC World Ceramics Congress, Montecatini Terme, Italy, Jun. 24-30, 1988 and in "Epitaxy of TiO$_2$ Thin Film on Sapphire by MOCVD", MRS Spring Meeting Symposium J, "Thin Film Structures and Phase Stability", San Francisco, Calif. Apr. 16-21, 1990, report the production of epitaxial titanium oxide films using MOCVD. In "Epitaxy of TiO$_2$ Thin Film on Sapphire by MOCVD" supra, the growth of epitaxial titanium oxide films on sapphire substrates by thermally decomposing titanium isopropoxide in the presence of oxygen in a cold wall low pressure MOCVD system is disclosed. In "Ceramic Epitaxial Films and Multilayers Prepared by MOCVD", supra, epitaxial titanium oxide and vanadium oxide films on sapphire substrates are produced using the MOCVD process for growth of the films in single and multilayer configurations. Titanium oxide and aluminum oxide films were deposited using molecular beam epitaxial methods in "Titanium Oxide Aluminum Oxide Multilayers Ceramic Thin Films", Alexander et al., *J.Am. Ceram. Soc.*, vol. 73(6), 1990. In "Epitaxial Thin Films of ZnO on Cds and Sapphire", *J. Vacuum Sci. and Tech.*, vol. 6, no. 1, 1968, Rozgonyi et al., discuss epitaxial films of ZnO, a non-rutile structured oxide, produced by sputtering on sapphire. Shiosaki et al, in "High Rate Epitaxial Growth of ZnO Films on Sapphire by Planar Magnetron Sputtering System", *J. Crystal Growth*, 45 (1978) 346-349 production of epitaxial films of ZnO were obtained on sapphire.

Additionally, the development of chemical sensors based on thin film technology is a rapidly growing area in chemical sensing. Thin film sensors offer the potential advantages of lower cost, greater sensitivity, less drift, and the achievement of selectivity by integrating different sensors on a single wafer for using semi-conductor microfabrication techniques. Key to development of such a technology is an understanding of what film characteristics are important for sensing and how to optimize processing to enhance those characteristics.

SUMMARY OF THE INVENTION

The present invention is directed to a thin film comprised of a planar epitaxial film of tin oxide having low defect density, high purity, rutile unit cell structure, one crystalline orientation, controlled stoichiometry, extended lateral dimensions, a high degree of atomic order extending to the surface of the film, extremely smooth surface morphology, and being colorless and transparent; and a method for producing the same. The present invention provides, inter alia, a gas sensor element comprised of a highly ordered planar epitaxial film of $SnO_2$ on an insulating substrate having a metal dispersed thereon and multi-element arrays comprised of a plurality of these sensor elements.

Advantages of the materials and methods according to the present invention include the possibility of using cleaner fabrication environments and constituent materials of high purity as opposed to prior art methods, as for example chemical vapor deposition methods, which use more complex materials and produce less pure films. Purity of the materials can be maintained and monitored. During the deposition process, existing quartz crystal monitoring technology can be used to monitor and control the deposition, thus, allowing the composition of films according to the present invention to be altered over relatively short (atomic) thicknesses for applications in which this type of material would be desirable. Most importantly, the present invention provides high quality, smooth films, exhibiting single crystal-like order in lateral dimensions greater than those of single crystals ($>1$ cm$^2$).

The significant and immediate value of films according to this invention with respect to chemical sensing includes provision of a superior material in thin or ultrathin film form which can be produced with a high quality, ordered nature and that can improve response characteristics of the sensor (speed, stability) by simplifying interactions with the environment being analyzed for composition. Additionally, the planar form of the materials is of high utility, especially as compared to bulk crystals, because it can be combined with existing know-how for device integration, and the fabrication method is well suited to scale-up. A collection of sensor array elements made of the thin film can be produced with varying response characteristics. When integrated onto a sensor chip and coupled with pattern recognition signal processing, arrays of such elements should be capable of composition analysis for mixtures at low cost. It is reasonable to expect the technology to affect the construction of both gas and solution chemical sensors. The ease with which miniaturization could be achieved using planar lithographic methods should also open up more sensing applications.

Another possible application of the films according to the present invention would be their use as large substrates in the production of highly ordered films of hydrocarbons by molecular self assembly. Such constructs could serve as sensor elements with selective monolayer terminations and in various modified forms they could also impact the areas of micro- and molecular electronics and corrosion.

The relatively large size of these crystal-like oxide films (compared to bulk single crystals) could make them valuable in areas like optics as well, including their use as coatings and transparent conductors.

BRIEF DESCRIPTION OF THE DRAWINGS

FIG. 1a shows, at 20,000× magnification, a film grown according to the present invention on sapphire (1102) at 500° C.; FIG. 1b shows, at 30,000× magnification, a film grown according to the present invention on sapphire (0001) at 500° C.; FIG. 1c shows, at 10,000× magnification, a film grown according to the present invention on $TiO_2$ (110) at 500° C.; and FIG. 1d shows, at 30,000× magnification, a textured film grown on sapphire (1102) at 30° C., as an example of a non-epitaxial film grown under conditions other than those described by the present invention. Bright objects visible in the micrographs are purposely imaged dust particles.

FIG. 2a shows a scan of a 1000Å film deposited on titanium oxide (110); FIG. 2b shows a scan of a 2500Å film on sapphire (1102); and FIG. 2c shows a scan of a 1000Å film on sapphire (0001).

In FIG. 5a, the sensor was subjected to gas-pump cycles of 0.1% $H_2$ in room air while at 125° C. In FIG. 5b the sensor was subjected to gas-pump cycles of 0.1% $H_2$ in dry air at 25° C. The gas-pump cycles are indicated by the arrows.

DETAILED DESCRIPTION OF PREFERRED EMBODIMENTS

Figure 1A:
FIGS. 1a–1d show scanning electron micrographs of tin oxide films which are grown on single crystal substrates having varying crystalline orientations.

The present invention pertains to a process for preparing highly ordered planar epitaxial films of tin oxide ($SnO_2$) which comprises cleaning and preparing an epitaxial grade substrate, slowly depositing a film of tin oxide on the substrate using reactive sputter deposition under vacuum conditions at a temperature greater than about 300° C., and preferably greater than about 500° C., gradually cooling the film in the process gases to ambient temperature, and optional subsequent treatments.

Single crystal substrates, polished to an epitaxial-grade surface finish are obtainable from commercial sources as for example Union Carbide, Insaco, Commercial Crystal, Inc. Substrates suitable for use in the present invention include various crystal cuts, including, but not limited to, titanium oxide $TiO_2$ (110), R-axis sapphire (1102) and C-axis sapphire (0001). For many, but not all applications, insulating substrates such as sapphire are preferred. An example of an application wherein an insulating substrate is preferred is use of the thin films according to the present invention as part of a chemical sensing device. Sapphire is a preferred insulating substrate because it is inert chemically and is a commercially viable material due to its moderate cost and its capability to have a high degree of surface finish. Additionally, sapphire, when properly cut, provides a nearly perfect lattice match in one crystalline direction with tin oxide (but not a perfect match in the other direction).

Wafers of "epitaxial grade" substrate are cut or scribed into sections or pieces having a dimension and thickness appropriate for the intended use of the film. The substrates are preferably mounted on a sample holder in a vacuum chamber that is preferably compatible with a base pressure of from less than about $10^{-9}$ to less than about $10^{-6}$ Torr. It follows that a vacuum pumping system capable of producing these pressures should be used. The lower pressures generally produce more optimal results. Epitaxy of the films produced according to the present invention is thought to be promoted by their deposition on exceptionally clean smooth substrate surfaces. The sapphire substrate samples can be cleaned prior to mounting them on the holder, by placing them in any suitable high purity, freshly mixed acid-based cleaner, as for example, aquaregia (standardized mixture of $HNO_3$ and $HCl$). The aqua regia is preferably at a temperature of from about 40° C. to about 80° C., and most preferably at about 50° C. Samples of $TiO_2$ substrate are preferably washed in any suitable organic solvent followed by an alcohol rinse, as for example acetone followed by methanol. The cleaned epitaxial grade substrate is then prepared by heating it in the vacuum to a temperature greater than about 300° C. and preferably at least about 500° C. The vacuum pressure is preferably from about $10^{-9}$ Torr to about $10^{-6}$ Torr with $10^{-9}$ Torr being preferred.

At this point, it is preferable to ensure substrate purity and surface order subsequent to cleaning and preparing by using x-ray photoemission spectroscopy (XPS) [or Auger electron spectroscopy], ion scattering spectroscopy (ISS) and low energy electron diffraction (LEED) measurements. Optimal cleanliness and/or surface finish are indicated by observation of a sharp LEED characteristic pattern of spots, and the absence of contaminants in surface composition measurements (x-ray photoemission spectroscopy and ion scattering spectroscopy).

In preferably the same vacuum atmosphere in which the preparation (vacuum annealing) of the substrate is performed, reactive sputter deposition is used to deposit a film of tin oxide on the substrate. The reactive sputter deposition is preferably carried out in an atmosphere which is made up of oxygen and argon. The oxygen and argon gases should preferably be of the highest possible purity and preferably should be approximately 99.999% pure. The gases should be supplied to the vacuum chamber via lines having valves to regulate flow. The chamber should have pressure gauges to monitor the partial pressures of the gases. The partial pressure of oxygen should be from about 1 to about 50 mTorr, with about 10 mTorr being preferred. The partial pressure of argon should be preferably from about 1 to about 50 mTorr with 10 mTorr being preferred. To obtain a film having a stoichiometry $SnO_x$, where $x=2$, it is preferable to use a mixture of argon and oxygen of equal partial pressures. To produce a stoichiometry with $x<2$, (which may be desirable in certain applications) and thereby obtain films of higher bulk conductivity, the partial pressure of oxygen should be less than the partial pressure of argon.

The sputter deposition should be carried out using a radio frequency (rf) sputter gun having a shutter and a radio frequency power supply/matching network or any other suitable sputter deposition apparatus. The sputter target is preferably high purity tin and most preferably tin having about 99.999% or higher purity, although other suitable targets, as for example $SnO_2$ can be used in an atmosphere having an oxygen partial pressure which is either lower than that enumerated above or totally absent.

To achieve a high degree of structural order and epitaxy, it is useful to carry out the reactive sputtering at very low deposition rates, for example, from about 1 to about 10Å per minute and preferably about 5Å per minute on substrates held to a temperature greater than about 300° C., preferably at least about 500° C. and preferably no greater than 800° C. The heteroepitaxy exhibited by the films on sapphire substrates may be particularly dependent on using relatively slow deposition rates. Additionally, slow rates may make it possible to grow the tin oxide films at lower temperatures which are generally less damaging to the substrate. The deposition is preferably carried out using a radio frequency (rf) excitation power level of from about 30 to about 100 W, and more preferably a power level of about 50 W.

The tin oxide film according to the present invention is preferably deposited on the substrate to a thickness of from about 200Å to about 2500Å. The actual thickness, whether within this range, thinner or thicker however, should be governed by the intended use for the film. Optical, electronic and structural characteristics can vary with film thickness and various applications will require differing film thicknesses. The method of the present invention is applicable for producing high quality epitaxial films over a wide range of thicknesses including the ultrathin regime.

The tin oxide film in principle can be deposited to any desirable lateral dimension and it is therefore possible to obtain films which are quite laterally extended, exhibit a single crystalline orientation and have an area which is greater than about 1 $cm^2$. Lateral extension of the films according to the present invention is theoretically limited only by the size of the substrate and of the vacuum chamber in which the deposition takes place.

In order to minimize strain-induced defects in the film, the film is preferably cooled gradually to ambient temperature and most preferably over a period of from about 30 to about 60 minutes. The cooling step is preferably done in the presence of the process argon and oxygen gases. Since there is a thickness dependence to the strain-induced defects, relatively thicker films (closer to about 2500Å) should be cooled even more slowly to avoid cracking.

The process of the present invention can further comprise altering the tin to oxygen stoichiometry on the surface of the film. Tailoring of the surface of the films can be used to affect a number of electronic, chemical and optical properties, thereby permitting the film material to be optimized for a number of different applications.

Altering the stoichiometry can be accomplished in various ways, including heating the film in oxygen, oxygen plasma treatment, heating the film in a vacuum, and sputter bombardment of the film in argon. Films in which the surface has been reduced, should preferably have a stoichiometry of approximately $SnO_{1.7}$.

Heating the film in oxygen in order to alter the surface tin to oxygen stoichiometry preferably comprises heating the film to a temperature of from about 400° C. to about 700° C., in a partial pressure of from about 0.1 to about 100 Torr for a period of from about 1 to about 10 minutes.

Oxygen plasma post-treatment of the film in order to alter the surface stoichiometry is preferably done by allowing from about 1 to about 100 mTorr of oxygen into the vacuum chamber in which the substrate is mounted. A radio frequency plasma is preferably "struck" by the application of from about 5 to about 50 W of radio frequency power to a metal band, preferably made of copper which has been wrapped around a glass tube connected to the vacuum chamber.

Alternatively, the stoichiometry can be altered by heating the film in a vacuum to a temperature of from about 400° C. to about 1000° C. for a time period of from about 1 to about 10 minutes.

Additionally, sputtering in argon can be used to alter the stoichiometry. Sputtering in argon comprises the sputter bombardment or etching of the film in an argon atmosphere in which an argon ion beam is used to remove or etch away material from the film.

Reference is made to "Preparation of well-ordered, oxygen-rich $SnO_2$ (110) surfaces via oxygen plasma-treatment", *J. Vac. Sci and Tech.*, A8 (3), May/June 1990 by Cavicchi et al., and "Oxygen vacancies and defect electronic states on the $SnO_2$(110)-1X1 surface", *Physical Review*, vol. 38, no. 3 July 1988 by Cox et al., contents of both of which are hereby incorporated by reference, for a further discussion of post-treatment methods as applied to single crystal tin oxide.

A thin film of the invention comprises a planar epitaxial film of $SnO_2$. Films of $SnO_2$ according to the present invention are characterized by having low defect density, high purity as indicated by X-ray photoelectron spectroscopy, futile unit cell structure as indicated by XRD, one crystalline orientation, stoichiometry of 1 tin to 2 oxygen (before surface modification, if any), extended lateral dimensions, and a high degree of atomic order extending to the surface of the film. The films have an extremely smooth surface morphology, are colorless and transparent and are thus optically clear.

A structure of the present invention can also include a substrate having a crystalline structure upon which the thin film is situated. Examples of suitable substrates include, but are not limited to, technologically important cuts of sapphire and titanium oxide.

Figure 2A:
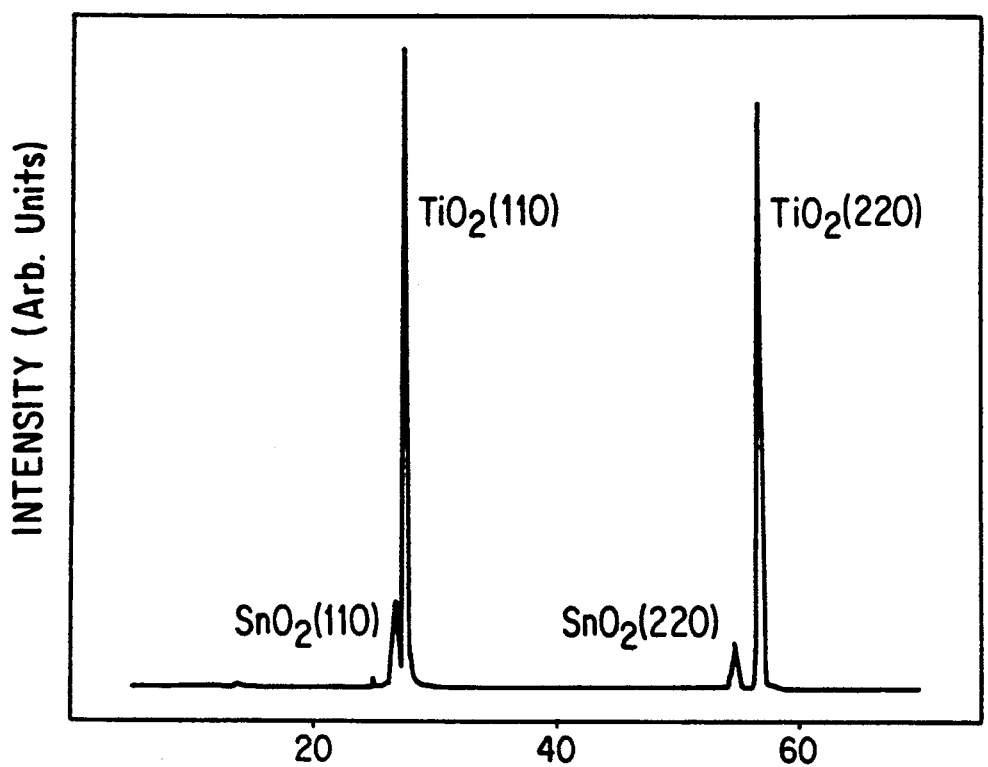
FIGS. 2a–2c show x-ray diffraction 2Θ scans for tin oxide films deposited on three different substrates.
Figure 2B:
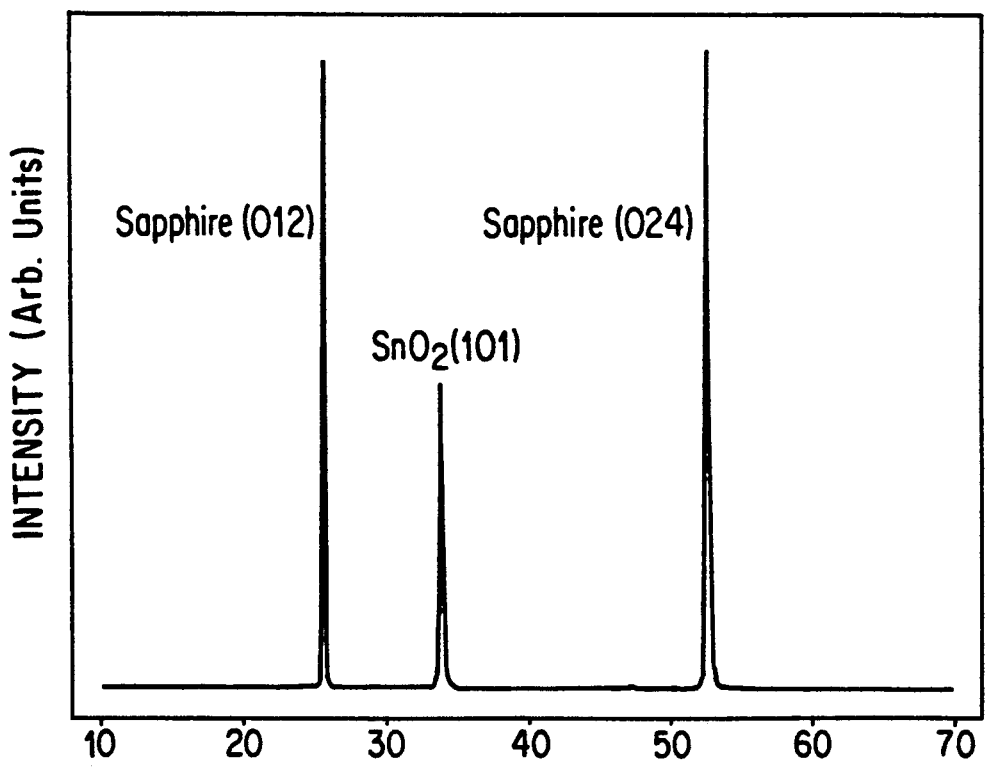
Figure 2C:
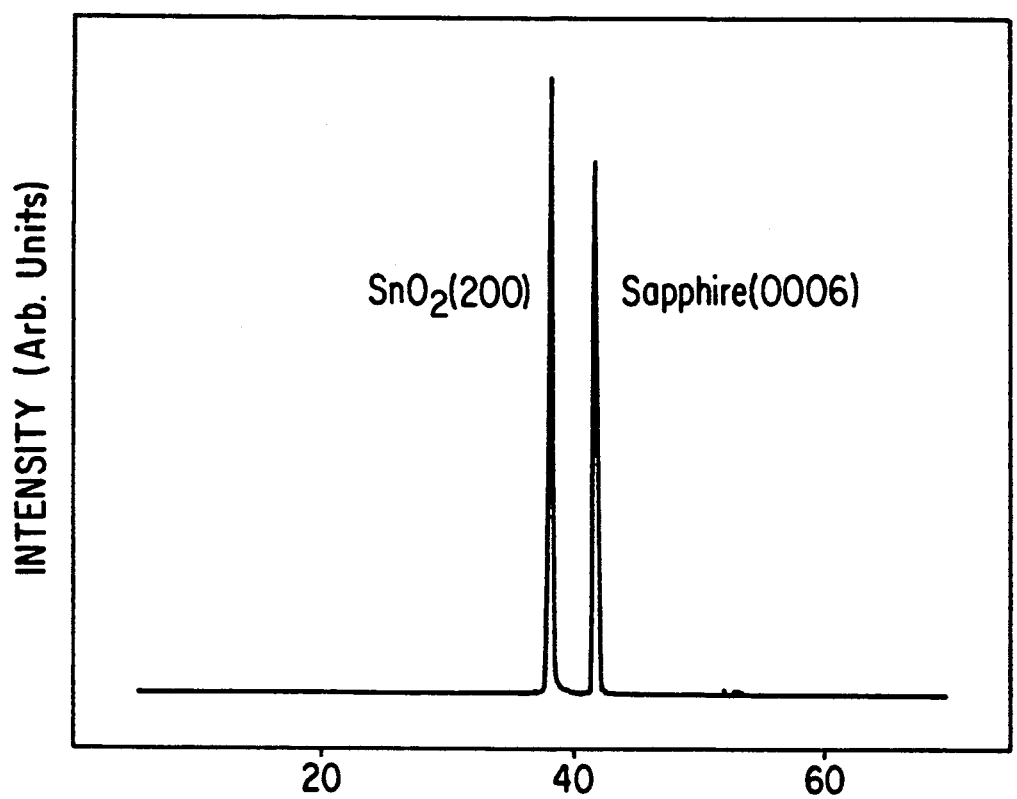

The thin film of the present invention may be characterized by single crystal orientation as evidenced by x-ray diffraction 2Θ scans. Films which have been deposited on sapphire (1102) substrates should preferably show only (101) film diffraction peaks, films on sapphire (0001) substrates should preferably show only (100) film diffraction peaks and films which have been deposited on $TiO_2$ (110) substrates preferably should show only (110) film diffraction peaks on x-ray diffraction scans. Reference is made to FIGS. 2a, 2b, and 2c wherein typical x-ray diffraction 2Θ scans are shown for films deposited on $TiO_2$ (110), sapphire (1102) and sapphire (0001), respectively.

Figure 3A:
FIGS. 3a–3f show low energy electron diffraction (LEED) patterns from the surface regions of the substrates (3a, $TiO_2$ (110); 3b, Sapphire (1102); 3c, sapphire (0001)), and $SnO_2$ films d-f respectively, grown on these substrates. These results demonstrate that the ordering of the various films is epitaxially related to the structure of the given substrate and that the order persists to the outermost layers.
Figure 3D:
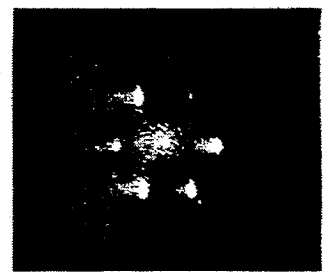
Figure 3B:
Figure 3E:
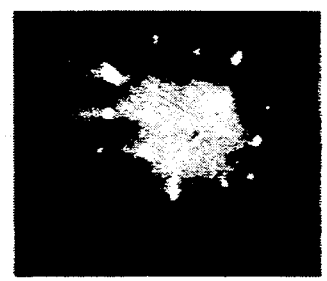
Figure 3C:
Figure 3F:

The structural ordering in films according to the present invention preferably extends to their surface as evidenced by low energy electron diffraction (LEED) measurements which probe the outermost ~25Å of the film and indicate ordering. FIG. 3 shows LEED results indicating registration between the crystalline structures of the substrates and the films which is observed across the entire film. LEED results are shown for three substrates (FIG. 3a, titanium oxide (110); FIG. 3b, sapphire (1102); and FIG. 3c, sapphire (0001) as compared to the films of $SnO_2$ which were deposited upon them respectively (FIGS. 3d, 3e, and 3f).

According to the present invention, films fabricated using equal partial pressures of oxygen and argon will exhibit bulk stoichiometries that are within 1% of $SnO_2$ according to secondary ion mass spectrometry (SIMS) measurements. The near surface stoichiometry of oxygen to tin is described by XPS. In this measurement, the ratio of oxygen 1s/tin $3d_{5/2}$ peak areas will preferably exhibit values from about 0.250 to about 0.300 when measured using a VG hemispherical analyzer. A lower partial pressure of oxygen relative to argon during fabrication will produce a film that has a lower oxygen content. High purity was indicated to the resolution of the spectroscopy (1 part per thousand "bulk" and 0.01 monolayer at the surface) in which no contaminants are observed in films deposited according to the present invention.

Using this invention, films with a wide range of conductance can be fabricated. Films fabricated using equal partial pressures of argon and oxygen will preferably be insulating. The surface stoichiometry of such films may be altered and made oxygen deficient by, for example, argon sputtering. This results in films that have a conductance which is greater than $10^{-4}$ mhos per square. Films fabricated using an oxygen partial pressure that is lower than the argon partial pressure will preferably have a conductance which is $10^{-4}$ mhos per square or higher, depending on the film stoichiometry.

Figure 1B:
Figure 1C:
Figure 1D:

Scanning electron micrographs of films according to the present invention should preferably reveal a smooth texture down to a level of magnification of 10,000×, preferably down to a level of about 30,000×, and most preferably down to a level of about 75,000×. Reference is made to FIG. 1 wherein SEM images from tin oxide films according to the present invention on 3 different substrates (FIG. 1a, sapphire (1102); FIG. 1b, sapphire (0001); and FIG. 1c, $TiO_2$ (110)) are shown. The micrographs show an absence of grain boundaries. Compare FIG. 1d which shows a film which is not produced in accordance with the present invention (at a temperature of 30° C.), wherein a granular surface structure is evident.

Atomic force microscopy (AFM) images give detailed surface structural information. The root mean square roughness (as measured by AFM) for films according to the present invention should preferably be from about 1 to about 20Å over an area of approximately 1 μm×1 μm. The peak to valley roughness (AFM) over the same area should preferably be from about 10 to about 120Å. Values specific to the various substrates should preferably be about 1.4Å rms roughness and about 14.3Å peak-to-valley roughness for films deposited on sapphire (1102) substrates; about 10Å rms roughness and about 60Å peak-to-valley roughness for sapphire (0001) substrates; and about 10Å rms roughness and about 90Å peak-to-valley roughness for $TiO_2$ (110) substrate.

A chemical sensor element may be comprised of a planar epitaxial film of $SnO_2$ according to the invention having a low defect density, high purity, stoichiometry of 1:2 Sn:O, extended lateral dimensions relative to single crystals, and a high degree of atomic order extending to its surface. The film is extremely smooth, colorless and transparent and is disposed on an insulating substrate. A metal, which may be, but is not limited to, iron, nickel, ruthenium, molybdenum, tungsten, niobium, copper, tantalum, silver, platinum or palladium, is dispersed on the tin oxide film. For example, in sensors in which it is desirable to detect hydrogen gas, the use of palladium is preferred.

While the inventors do not wish to be bound by any one theory, it is hypothesized that it is the heteroepitaxy of these films which is exhibited on sapphire, that is useful in chemical sensors and sensing arrays. The significance and immediate value of this invention with respect to chemical sensing includes: (1) a superior material in thin or ultrathin form is produced with a high quality, ordered nature that can improve response characteristics of the sensor such as speed or stability by simplifying interactions with the environment being analyzed for composition, (2) the planar form developed is of high utility especially as compared to presently available bulk crystals because it can be combined with existing know-how for device integration, and (3) the fabrication method is well-suited to scale-up.

Figure 4:
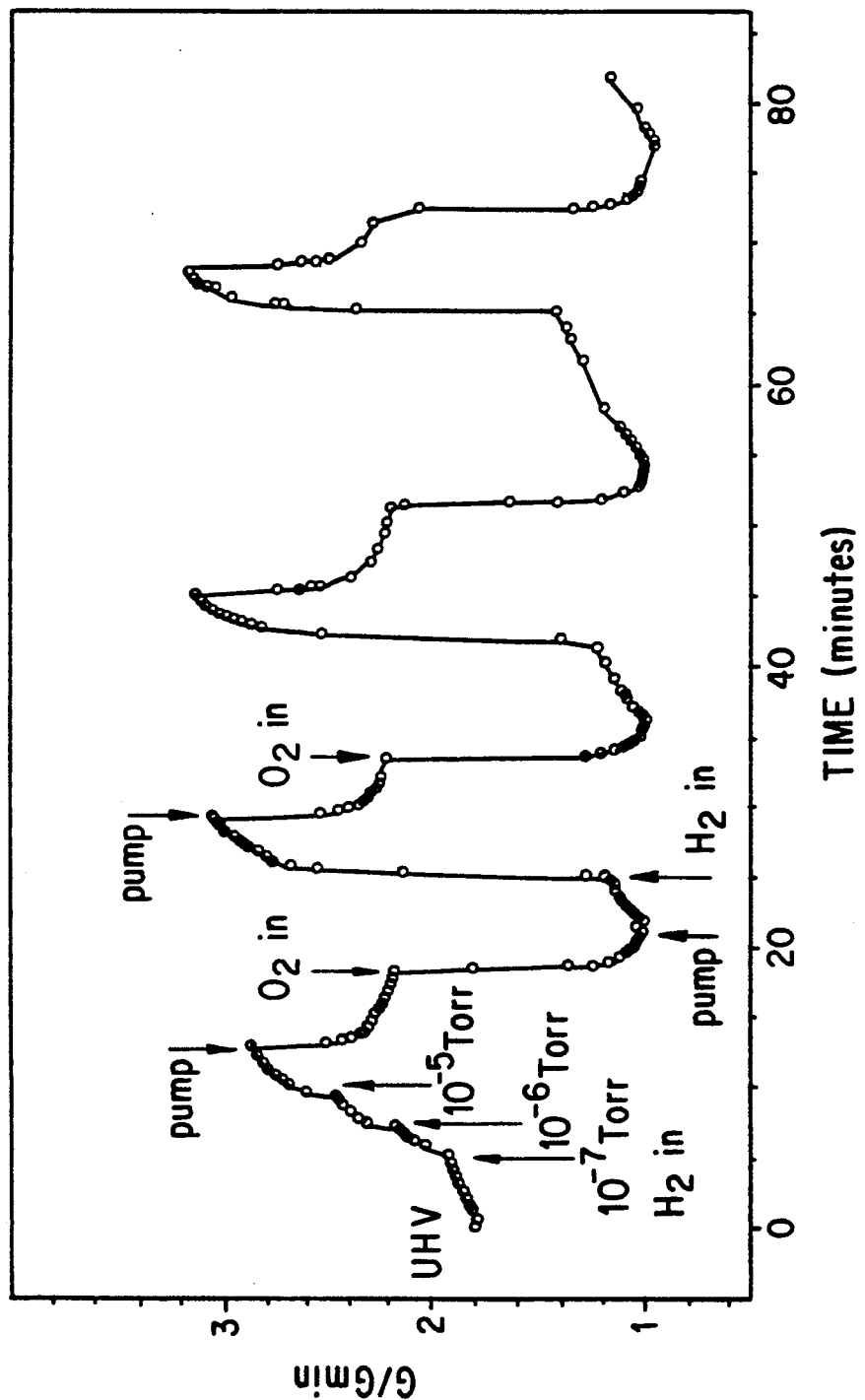
FIG. 4 shows the conductance response (G/Gmin), (the ratio of the measured conductance to the minimum conductance value of the sequence) produced by the indicated $H_2$-pump-$O_2$-pump cycles for a Pd-$SnO_2$ gas sensor according to the present invention, fabricated using an $SnO_2$ film deposited on sapphire (1102).
Figure 5A:
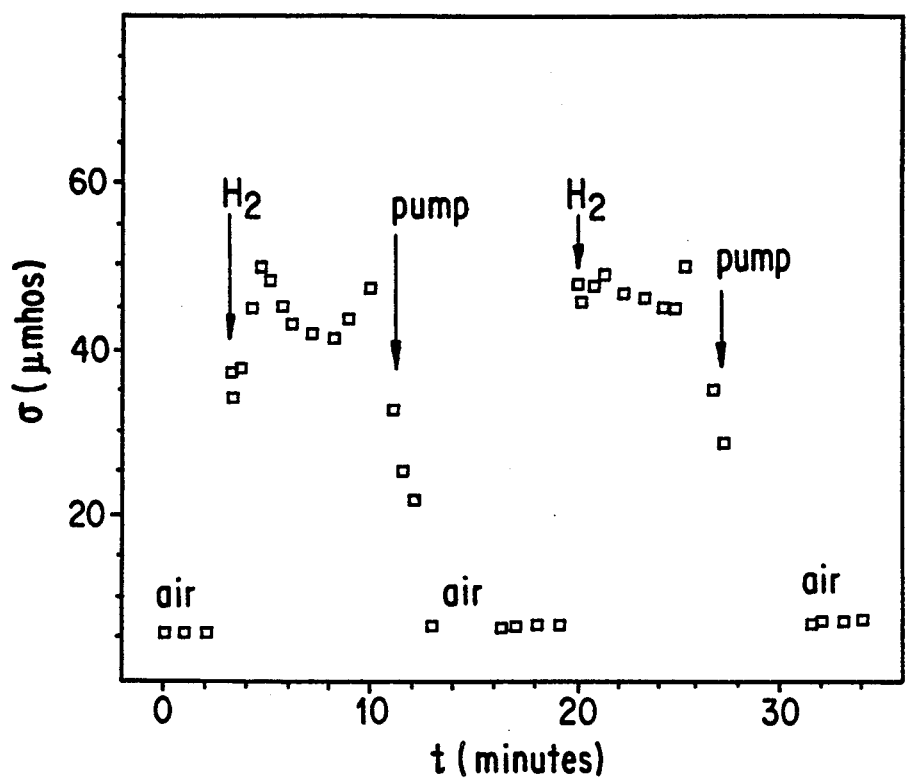
FIGS. 5a and 5b show sensing response measurements for the same Pd-$SnO_2$ film sensor as in FIG. 4.
Figure 5B:
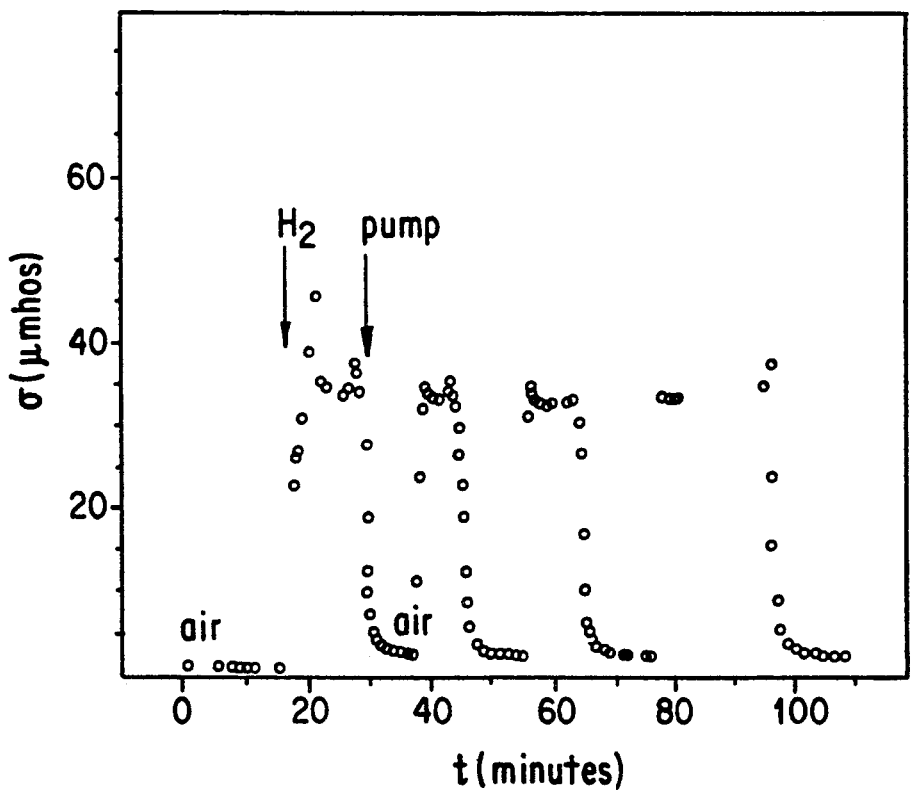

Referring to FIG. 4, a gas sensor element according to the present invention may be formed by in situ evaporation of small palladium islands with an equivalent thickness of at least one, preferably three monolayers onto a 320Å $SnO_2$ (101) film on (1102) sapphire. The conductance changes (sensing action) produced in the presence of the indicated cycled exposures to oxygen and hydrogen are expressed as the instantaneous conductance divided by the minimum conductance value observed for the sequence. Prior to these measurements, the $SnO_2$ film was thermally oxidized in situ in 1 Torr of oxygen at 425° C. and then exposed to a three monolayer equivalent dose of palladium. FIGS. 5a and 5b show sensing response measurements for 0.1% hydrogen in air under more practical atmospheric pressures. The relatively low hydrogen presence in air is easily detected, and differences are illustrated relating to temperature and the presence of moisture. Conductances in all cases were measured using a retractable ultrahigh vacuum compatible 4-point probe described in *J. Vacuum Sci. and Tech.*, Vol. A5, 1987, pp. 115-117. Conductance measurements can be easily adapted to a hardwired device configuration.

The results as indicated by FIGS. 4, 5a and 5b demonstrate the behavior and functioning of a single $SnO_2$ film-based sensor element. This invention can be used to produce a multi-element sensor array by lithographic methods with greatly increased sensing capability and the ability to analyze mixtures. Multi-element arrays composed of a plurality of chemical sensor elements in accordance with the present invention can be made in which the film is comprised of isolated sections comprising different metals dispersed upon each section for detecting different gases, for example, iron is sensitive to oxygen, palladium is sensitive to hydrogen, etc. Techniques known in the lithographic art may be used, as for example, the reactive etching technique as described by Chang et al. in "Tin Oxide Microsensors", *J. Proceedings of* 1985 *International Conference on Solid State Sensors and Actuators,* Phila., Pa. IEEE, Piscataway, N.J. Other suitable methods by which multi-element sensor arrays can be made include photolithography, chemical etching, X-ray and electron beam lithography, plasma etching, and physical masking.

The following examples are illustrative in nature and are not intended to limit the scope of the invention in any way. Other equivalent methods of practicing the present invention may occur to those skilled in the art upon reading the present specification.

EXAMPLES

Methods and Materials

Reactive sputtering (RS) using radio frequency (rf) excitation is carried out in an all-stainless steel-copper gasket-sealed vacuum chamber which is compatible with a base pressure of less than $10^{-9}$ Torr. The vacuum pumping system is capable of producing an ultimate pressure of $10^{-9}$ Torr and includes a cryosorption (roughing) (MDC) and a cryopump (Varian) having a pumping speed as follows: 1050 liter/sec nitrogen, 1200 liter/sec argon, 2200 liters/sec hydrogen, and 4000 liters/sec. water. A holder for the substrate sample with a temperature control for heating in oxygen up to 600° C. is mounted inside the vacuum chamber. The chamber is equipped with Cajon-type seal lines for introducing oxygen and argon gases. A pressure monitor for measuring gas pressures of the ion gauge type (Varian) is used and a precision capacitance manometer (MKS) is also included. The sputter gun used is a 1 inch target ultrahigh vacuum compatible, with shutter and a radio frequency power supply/matching network (U.S. Gun). The sputter target (source material) is 99.999% pure tin (Cerac). Sputtering is carried out in flowing high purity (99.9995%) argon and oxygen (99.997%) each with equal partial pressures of 10 mTorr. Sample heating is accomplished using a platinum foil resistance heater and temperatures are characterized with both thermocouple and optical pyrometer measurements. Deposition thickness is monitored with a quartz crystal oscillator sensor (Leybold Heraus), calibrated using a step profiler. The system includes a retractable four point conductivity probe as described in *J. Vacuum Sci. and Tech., supra*, to provide conductivity data in situ after deposition.

Surface analyses of the films are carried out in a separate ultrahigh vacuum (UHV) system with separate chambers for sample treatment and analysis. A translation/rotation stage is used to transfer samples between chambers without breaking vacuum. Compositional analyses are obtained using x-ray photoemission spectroscopy (XPS) and ion scattering spectroscopy (ISS) (VG ESCALAB Mark II). ISS is sensitive to the outermost atomic layer, while XPS samples to depths of approximately 20-50Å. Valence band states of the materials are investigated with ultraviolet photoemission spectroscopy (UPS). Surface structural information is obtained with low energy electron diffraction (LEED). Conductivity changes are monitored in situ using a retractable four-point probe. Ex-situ film characteristic analyses including x-ray diffraction (XRD), and scanning electron microscopy (SEM), atomic force microscopy (AFM) and secondary ion mass spectrometry (SIMS) are also performed.

EXAMPLE 1

Film Preparation

Single crystal sapphire (1102) and (0001) oriented substrates polished to an "epitaxial-grade" surface finish are obtained from Union Carbide. The sapphire samples are cleaned using high-purity, freshly mixed aqua regia at 50° C. Polished titanium oxide (110) samples (Commercial Crystal, Inc.) are cleaned with acetone and methanol. XPS shows carbon contamination in all samples as mounted following solution cleaning, while LEED patterns generally have high background intensities.

The samples are mounted on holders in the vacuum chamber, the chamber is pumped out and the substrates are heated in the vacuum to 500° C. Careful control of the temperature is achieved using a computer controlled feedback circuit. Annealing in vacuum to 500° C. is effective at removing carbon from the substrates and enhancing the contrast of LEED patterns, and is used to clean the substrates before deposition. Oxygen and argon are flowed through the chamber by throttling the cryopump valve and opening the gas lines to produce a flow of the respective gases. Oxygen and argon are each used at a partial pressure of 10 mTorr.

Power is applied to the sputter gun with a tin target mounted upon it. Films prepared by reactive sputtering (RS) are deposited on each of 3 substrates [sapphire (1102), sapphire (0001), and $TiO_2$ (110)] at a temperature of 500° C. to a thickness of approximately 200Å to 2500Å. The shutter is closed when the desired thickness is reached. The deposition rate is about 5Å per minute at a rf excitation level of 50 W. The sample is cooled to ambient temperature over the course of 1 hour in an environment which is comprised of the process oxygen and argon gases. The gas line valves are closed, the chamber is vented and the substrate samples are removed.

Results

SEM micrographs (FIGS. 1a, 1b, 1c) of films grown on the 3 different substrates show smooth, featureless morphology (except for the purposely imaged dust particles) down to a level of magnification of 30,000×.

LEED patterns (FIG. 3) probing the outermost ~25Å of the films show spot patterns. The LEED patterns represented in FIG. 3 show that the films take on an orientation related to their respective substrates.

Analyses of the oxygen and tin concentration ratios as determined by comparisons between films according to the present invention and bulk single crystal $SnO_2$, are measured using XPS and SIMS. A stoichiometry of $SnO_2$ is determined.

Atomic force microscopy (AFM) images are used to characterize the films with the following results over a 1 μm × 1 μm area:

|  | rms roughness | peak-to-valley |
| --- | --- | --- |
| $SnO_2$/sapphire (1102) | 1.4 Å | 14.3 Å |
| $SnO_2$/sapphire (0001) | 10 Å | 60 Å |
| $SnO_2$/$TiO_2$ (110) | 10 Å | 90 Å | rms = Root mean square

EXAMPLE 2

A film is deposited on a sapphire (1102) substrate in accordance with the procedure detailed in Example 1 and left in the vacuum chamber in which deposition took place.

In a vacuum of ~$10^{-9}$ Torr, the film is annealed to 500° C. for 3 minutes. The film surface is thermally oxidized by introducing high purity oxygen (>99.997%, Matheson) into the chamber through a precision leak valve (Varian) to a pressure of 1 Torr. The film is then heated to approximately 425° C. for 3 minutes. The film is allowed to cool in the 1 Torr oxygen atmosphere to a temperature of 25° K. The oxygen is then pumped out to attain a vacuum of $10^{-9}$ Torr.

Palladium is deposited on the film from an ultrahigh-vacuum-compatible evaporator consisting of a resistive, braided tungsten filament element charged with high purity (99.997%) palladium wire pieces (Johnson Matthey, 0.25 mm diameter x ~3 mm) that are twisted onto the tungsten filament. To assure the highest purity of the source palladium, it is outgassed prior to deposition on the $SnO_2$ film by heating the filament in the vacuum for more than one hour in order to remove any absorbed gases. Prior to actual deposition on the film, the palladium deposition rate is measured by depositing it onto a calibrated quartz crystal monitor (Leybold Hereus). When outgassing is completed and the proper rate of deposition is obtained (~1 palladium monolayer equivalent per minute) the shutter on the evaporator is closed and the film is moved to the deposition position. The shutter is opened and at a rate of ~1 monolayer equivalent of palladium per minute the Pd is deposited until 3 monolayer equivalents (as islands) are deposited on the now ambient temperature $SnO_2$ film, at approximately 30° C.

Following deposition, the Pd/$SnO_2$/sapphire specimen is annealed in a vacuum of $10^{-9}$ Torr to 225° C. for 3 minutes to stabilize the morphology of the palladium dispersion. The specimen is then allowed to cool to approximately 25° C. in the vacuum.

Baseline conductance for the model sensor is measured in accordance with the following. The specimen is heated to a sensing measurement temperature (~125° C.). An ultrahigh vacuum-compatible 4-point conductance probe (*J. Vacuum Sci. and Tech., supra*) with spring loaded contact tips is moved into contact with the Pd/$SnO_2$ surface. There are 4 contact points in one row, equally spaced.

Conductance values are recorded by supplying to the specimen from a Keithley current source, a current of $10^{-5}$ amps through the outermost pair of contact tips and measuring the voltage drop between the innermost pair of contact tips. The baseline conductance is measured for a period of approximately 7 minutes while the sample is maintained at 125° C. in a vacuum of $10^{-9}$ Torr.

The baseline vacuum period is followed by gas-pump cycling periods during which sequential conductance measurements are made approximately every 15 seconds. FIG. 4, wherein all sensor test cycles were run on specimens held to 125° C., shows cycles consisting of first admitting $H_2$ in the chamber to a pressure of about $10^{-5}$ Torr, as measured by a calibrated remote ion gauge, through a leak valve. This first dose was admitted at sequentially higher pressures from $10^{-7}$ to $10^{-5}$ Torr. After a period of approximately 7 minutes, the leak valve to the $H_2$ is closed and $H_2$ is pumped out, resulting in a return to vacuum conditions. An $O_2$ dosing pump cycle is carried out by repeating the procedures as detailed for $H_2$, using an $O_2$ charged section that leads through a properly evacuated tube to the same system-mounted leak valve. FIG. 4 shows four such $H_2$-pump-$O_2$-pump cycles following the vacuum lead up baseline.

Additional runs involving $H_2$ injection in various air mixtures are performed, the results of which are shown in FIG. 5. FIG. 5(a) shows the effects at 0.1% $H_2$ in room (moist-humidity~30%) air. The specimen is maintained at 125° C. The conductance is measured as described above. The specimen was initially exposed to air at atmospheric pressure. The valves connected to the vacuum pumps are closed. A small amount of $H_2$-air mixture is let into the chamber through a leak valve to give a total $H_2$ concentration of 0.1%. After approximately 7 minutes, the valves connected to the pumps are opened and the entire chamber is pumped to a pressure of less than $10^{-7}$ Torr. The valves to the pumps are closed and air is let into the chamber at atmospheric pressure. FIG. 5(a) shows two such cycles.

FIG. 5(b) shows the results from a sensor test according to the procedure for 5(a) except that the sample is maintained at 25° C. and dry (moisture-free) air is used. Four cycles of gas exposures are shown indicating that the sensor element can sense $H_2$ at room temperature, without heating the sensor.

What is claimed is:

1. A thin film structure comprising:
    a smooth planar epitaxial film of $SnO_2$ having low defect density, rutile unit cell structure, one crystalline orientation, controlled stoichiometry, extended lateral dimensions as compared to single crystals, atomic order extending to the surface of said film and being of extremely smooth surface morphology, colorless and transparent.

2. The structure according to claim 1, further comprising a substrate having a crystalline structure on which the film is situated.

3. A thin film structure comprising:
    a smooth planar epitaxial film of $SnO_2$ having low defect density, rutile unit cell structure, one crystalline orientation, controlled stoichiometry, extended lateral dimensions as compared to single crystals, atomic order extending to the surface of said film and being of extremely smooth surface morphology, colorless and transparent; and
    a crystalline substrate selected from the group consisting of sapphire (1102), sapphire (0001) and $TiO_2$ (110) on which the film is situated.

4. The structure according to claim 3, further characterized by having by x-ray diffraction 2Θ scans of (100) film diffraction peaks on sapphire (0001), (110) film diffraction peaks on $TiO_2$ (110), and (101) film diffraction peaks on sapphire (1102); having orientational registration between the crystalline structures of the substrate and the film extending to the surface of the film as shown by low energy electron diffraction (LEED) studies; atomic force microscopy (AFM) indicating root means square (rms) roughness of from about 1 to about 20Å over an area of about 1 $\mu m \times 1$ $\mu m$ and a peak to valley roughness over the same area from about 10 to about 90Å, x-ray photoelectron spectroscopy (XPS) oxygen 1s/tin $3d_{5/2}$ peak area ratios as measured using a VG hemispherical analyzer of from about 0.250 to about 0.300, a lateral dimension greater than about 1 cm$^2$, and a bulk stoichiometry of $SnO_2$ as measured by SIMS.

5. The structure according to claim 4, wherein the substrate is sapphire (1102) and AFM scans indicate root mean square roughness of about 1.4Å and peak to valley roughness of about 14.3Å.

6. The structure according to claim 4, wherein the substrate is sapphire (00012) and AFM scans indicate a root mean square roughness of about 10Å and a peak to valley roughness of about 60Å.

7. The structure according to claim 4, wherein the substrate is $TiO_2$ (110) and AFM scans indicate a root mean square roughness of about 10Å and a peak-to-valley roughness of about 90Å.

8. The structure according to claim 2, wherein said substrate is insulating, and further comprising:
    at least one monolayer equivalent of metal dispersed on the film of $SnO_2$.

9. The structure according to claim 8, wherein at least 3 monolayer equivalents of said metal are dispersed on the film.

10. A thin film structure comprising:
    a smooth planar epitaxial film of $SnO_2$ having low defect density, rutile unit cell structure, one crystalline orientation, controlled stoichiometry, extended lateral dimensions as compared to single crystals, atomic order extending to the surface of said film and being of extremely smooth surface morphology, colorless and transparent;
    an insulating substrate having a crystalline structure on which the film is situated; and
    at least 3 monolayer equivalents of a metal selected from the group consisting of iron, nickel, ruthenium, molybdenum, tungsten, niobium, copper, tantalum, silver, palladium and platinum.

11. The structure according to claim 10, wherein said metal is palladium.

12. A chemical sensor element comprising:
    a smooth planar epitaxial film of $SnO_2$ having low defect density, rutile unit cell structure, one crystalline orientation, controlled stoichiometry, extended lateral dimensions as compared to single crystals, atomic order extending to the surface of said film and being of extremely smooth surface morphology, colorless and transparent;
    an insulating substrate having a crystalline structure on which the film is situated; and
    at least one monolayer equivalent of metal dispersed on the film of $SnO_2$.

13. A plurality of chemical sensor elements, comprising:
    a smooth planar epitaxial film of $SnO_2$ having low defect density, rutile unit cell structure, one crystalline orientation, controlled stoichiometry, extended lateral dimensions as compared to single crystals, atomic order extending to the surface of said film and being of extremely smooth surface morphology, colorless and transparent;
    an insulating substrate having a crystalline structure on which the film is situated; and
    a plurality of at least one monolayer equivalent of metal dispersed on the film of $SnO_2$.

14. The chemical sensor according to claim 12, wherein said chemical is hydrogen gas or oxygen gas.

* * * * *